Figure 1:
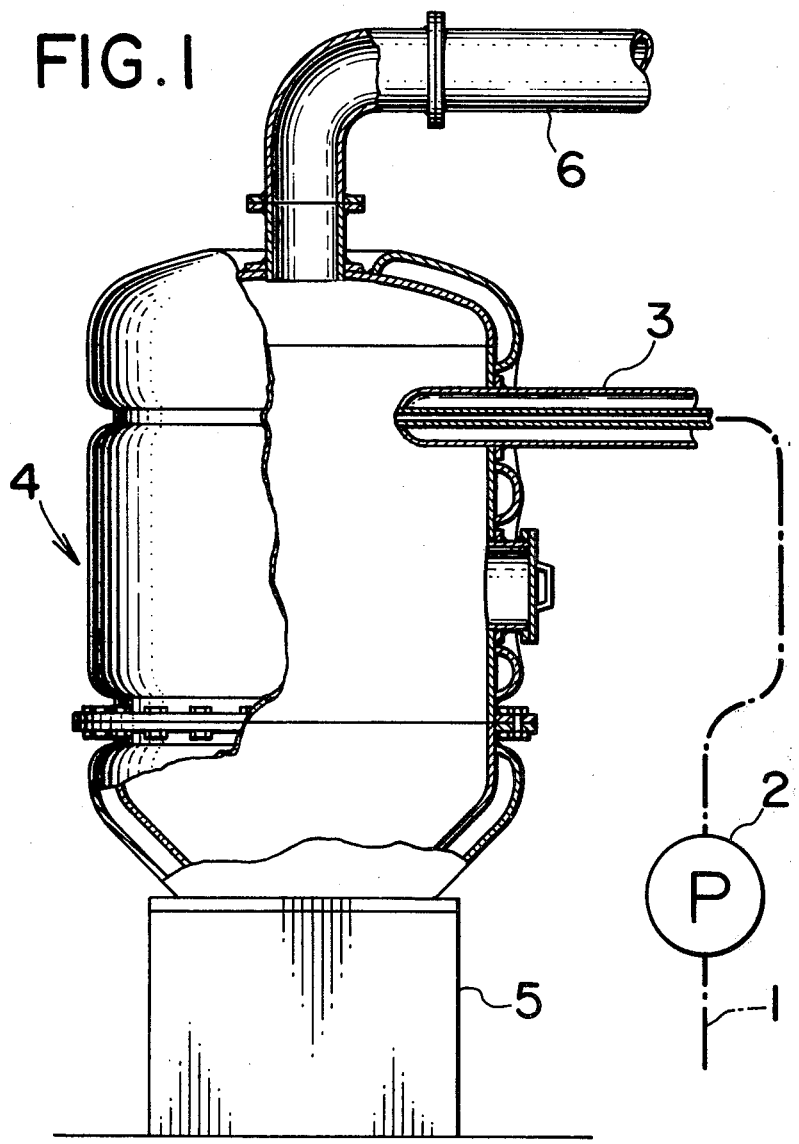

United States Patent [19]

Maekawa et al.

[11] 4,138,424

[45] Feb. 6, 1979

[54] METHOD FOR REMOVING TAR FROM CRUDE TOLYLENE DIISOCYANATE

[75] Inventors: Yoshihiro Maekawa, Nara; Masatoshi Matsuura, Hirakata, both of Japan

[73] Assignee: Orient Chemical Industries, Ltd., Osaka, Japan

[21] Appl. No.: 815,295

[22] Filed: Jul. 13, 1977

[51] Int. Cl.$^2$ .................... B01D 3/06; C07C 119/048
[52] U.S. Cl. ................................ 260/453 SP; 203/88
[58] Field of Search ...................... 260/453 SP; 203/88

[56] References Cited

U.S. PATENT DOCUMENTS

| | | | |
|---|---|---|---|
| 3,169,141 | 2/1965 | Kober et al. | 260/453 SP |
| 3,405,040 | 10/1968 | Ewald | 203/88 |
| 3,457,291 | 7/1969 | Baylor | 260/453 SP |

FOREIGN PATENT DOCUMENTS 1117066  6/1968  United Kingdom.

*Primary Examiner*—Dolph H. Torrence
*Attorney, Agent, or Firm*—Oblon, Fisher, Spivak, McClelland & Maier

[57] ABSTRACT

A method for removing tar from crude tolylene diisocyanate comprises quantitatively feeding a starting solution consisting of crude tolylene diisocyanate containing tar or its mixture with an inert organic solvent into the inlet of an elongated heating tube, thereby producing annular shape stream or spray stream of the starting solution in the region on the outlet of the heating tube, spouting the starting solution in this state from the outlet of the heating tube into a separation chamber kept at reduced pressure and thereby recovering tar in the form of nonviscous and porous masses from the starting solution.

4 Claims, 8 Drawing Figures

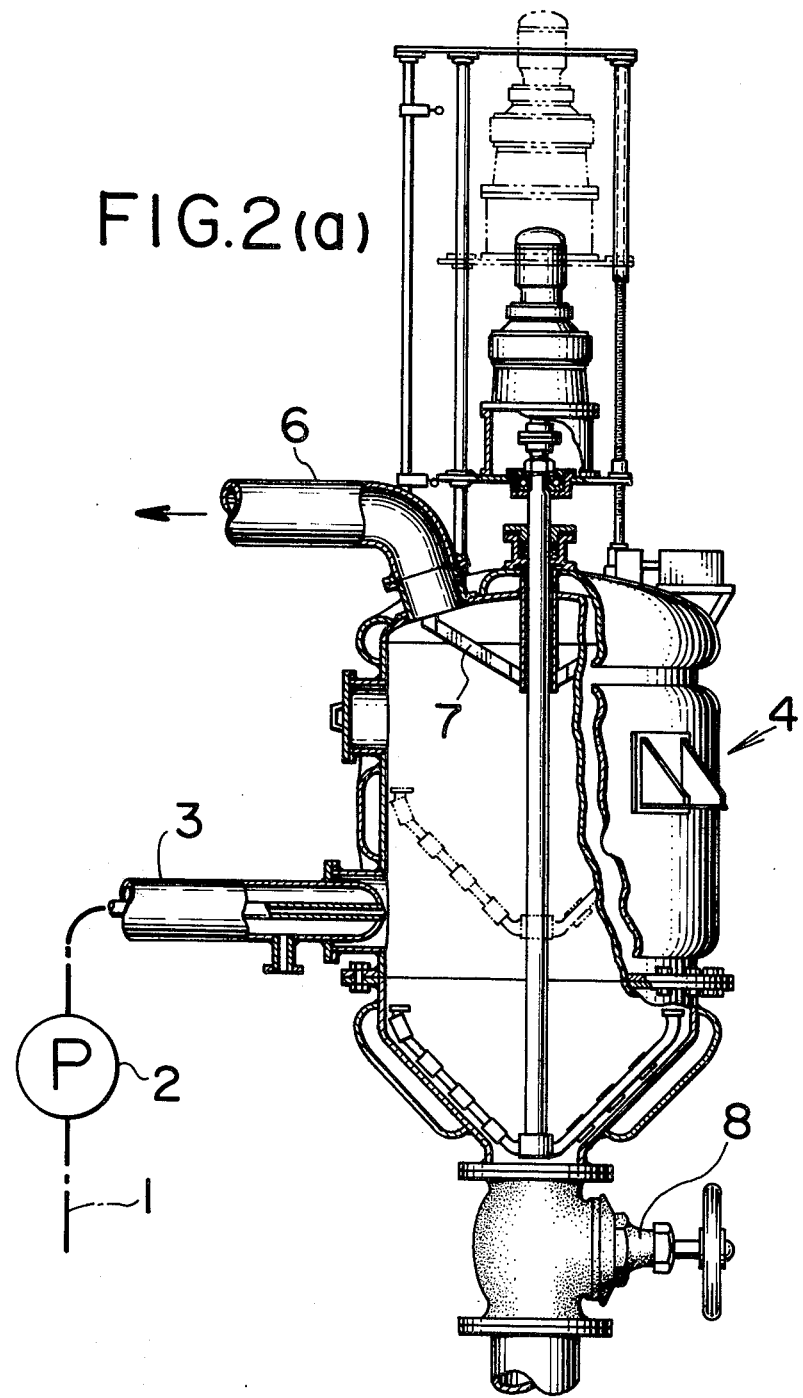

METHOD FOR REMOVING TAR FROM CRUDE TOLYLENE DIISOCYANATE

The present invention relates to a method for removing tar from crude tolylene diisocyanate.

Tolylene diisocyanate (hereinafter referred to as TDI) is the main raw material for preparing polyurethane and an important substance to be used as raw materials for various kinds of synthesized organic substances, fabric treating agents, adhesive agents and paints. However, industrially manufactured crude TDI usually contains a fair amount of tar (referred to as TDI tar) as impurities, and therefore the removal of tar therefrom is necessarily required.

However, no effective and economical method for removing TDI tar from crude TDI has been developed yet. At present, TDI tar containing several tens % of TDI is burnt up without any effective use of TDI, the amount of such TDI burnt up in a year in Japan reaching about several ten thousand tons.

The main cause to lower the efficiency in refining crude TDI is probably that crude TDI becomes extremely viscous with the decrease of the TDI content in TDI tar. According to the conventional method, the most efficient of the industrially applicable methods is only to remove TDI tar which still contains several tens % of TDI, as abovementioned. For example, in the operation of removing TDI tar from crude TDI using a conventional thin film evaporator, when TDI content in the TDI tar is lowered below several tens %, the viscosity of TDI tar extremely increases and not only the evaporation capacity is extremely lowered but disadvantageously TDI tar cannot be discharged from the evaporator.

Further, in the operation of recovering TDI from crude TDI by applying batch system vacuum concentration, the viscosity of TDI tar increases to extremely lower the evaporation with the decrease of TDI content in the TDI tar, and if the heating temperature is raised in order to solve the abovementioned difficulty, TDI tar and TDI are apt to be decomposed to generate a large amount of gas, possibly resulting in the danger of explosion.

As apparent from above, it is impossible according to the conventional method to separate TDI tar of little TDI contents economically and efficiently from crude TDI, and therefore TDI tar which has been concentrated to lower its TDI content to 15–40% is solidified by cooling, pulverized and burnt up at the present stage.

In view of the above, the object of the present invention is to provide a method for economically and efficiently removing TDI tar containing substantially no TDI from crude TDI.

A method according to the present invention comprises quantitatively feeding a starting solution consisting of crude TDI (defined as a mixture of TDI and TDI tar here) or its mixture with an inert organic solvent preferably of low boiling point into the inlet of an elongated heating tube so dimensioned as to have the ratio of its tube length to its inner diameter in a range from about 200 to about 5000 and heated above 230° C., thereby producing annular shape stream or spray stream of TDI tar containing substantially no TDI, vapor of TDI and organic solvent if any at the outlet of the heating tube, spouting the starting solution in this state from the outlet of the heating tube into a separation chamber kept at reduced pressure below 200 torr, and thereby recovering tar as nonviscous and porous masses from the starting solution while TDI and the organic solvent if any being substantially thoroughly recovered by evaporation.

It is surprising that according to the present invention, TDI tar containing substantially no TDI can be separated and obtained in the form of nonviscous and porous masses (of specific gravity below 0.5) which can be easily pulverized.

Generally, the state of the starting solution changes sequentially as follows. The starting solution fed into the heating tube is supplied with sensible heat in a sensible heat supply zone to reach its boiling point; it is further supplied with evaporation latent heat to evaporate the volatile substances and the vapor generated is included as fine bubbles in the solution in a bubble zone; the evaporation further proceeds and the bubbles grow to form plug-like shape in a plug zone; the vapor further increases in amount so that it moves forward through the solution while violently stirring the solution in a turbulence zone; the vapor further increases in amount so that the bubbles are communicated with one another to form large bubbles, which are sometimes torn to move forward pulsing in a pulse zone; the evaporation further proceeds so that the vapor flows at high speed through the central portion of the tube with the solution driven away toward the inner wall of the tube to form a stream of annular cross section in an annular shape stream zone; and the evaporation further proceeds so that unvolatile material is pealed off from the inner wall of the tube to move forward through the tube in spray in a spray stream zone.

The inventor has found after thorough study that in order to effectively treating crude TDI using an elongated heating tube, it is necessary to produce the abovementioned annular shape stream or spray stream of TDI tar in the region of the outlet of the tube opening to a separation chamber, and the present invention is based on this finding.

In the present invention, a further attention is to be paid to the fact that TDI tar, which is thought in general to be of high consistency or high viscosity at normal temperature, can be obtained as easily pulverable nonviscous masses a short time after spouting thereof into the separation chamber according to the present invention. Though the detail of the mechanism is not known, it is estimated to depend on the mechanism of the rise of the melting point of TDI tar caused by the decomposition of TDI tar itself, as well as on the rapid evaporation and the associated sudden temperature drop of TDI tar.

In view of the above, to produce a proper annular shape stream and spray stream of TDI tar at the outlet of the heating tube to obtain foamed masses of low specific gravity e.g. about 0.2 the composition of the starting solution, the ratio between the length and the inner diameter of the heating tube, heating temperature, the vacuum degree in the separation chamber and other conditions should be properly selected. And according to one aspect of the present invention, an example of the combination of practically effective operating conditions is as follows;

ratio of length/inner diameter of heating tube: 1500
heating temperature: 300° C.
vacuum degree in separation chamber: 5 torr On the other hand, in the process of thermally separating crude TDI, the state of separated TDI tar is of importance, as well as the increase of the heat supply efficiency, and the difficulty in this respect has been one of the decisive causes to prevent the rise of the separation efficiency in the conventional method as abovementioned. On the contrary, the present invention provides the following advantageous solution to this problem.

According to a preferred embodiment of the present invention, an annular or spray shape stream of viscous TDI tar containing substantially no TDI can be obtained at the outlet of the heating tube, which is extended by the effect TDI vapor stream in axial direction of the heating tube to project into the reduced pressure separation chamber, momentarily cooled to solidification by the adiabatic expansion of a very small amount of TDI vapor contained in the TDI tar in the separation chamber and is discharged in the form of nonviscous, porous and hollow cylindrical small masses. Since there occurs neither adhesion of TDI tar to the inner wall of the separation chamber and the peripheral portion of the outlet nor its mass formation which causes the apparatus to be inoperative, effective successive operation can be carried out thereby facilitating to take out the resulting substances.

The relief of the small masses of TDI tar is effected through falling by its own weight or by a proper scrubbing means provided near the outlet.

According to another preferred embodiment of the present invention, by opening the outlet of the heating tube into the bottom portion of the separation chamber of large capacity, to our astonishment, nonviscous and porous TDI tar is continuously accumulated upward from the bottom of the separation chamber to form a highly porous accumulated mass. This accumulated mass, being easily pulvable, is pulverized by a preliminarily provided means at a proper time, preferably after recovery of the normal pressure in the chamber, and discharged.

A preferred embodiment of the present invention will now be described in detail with reference to the appended drawings.

Figure 2:
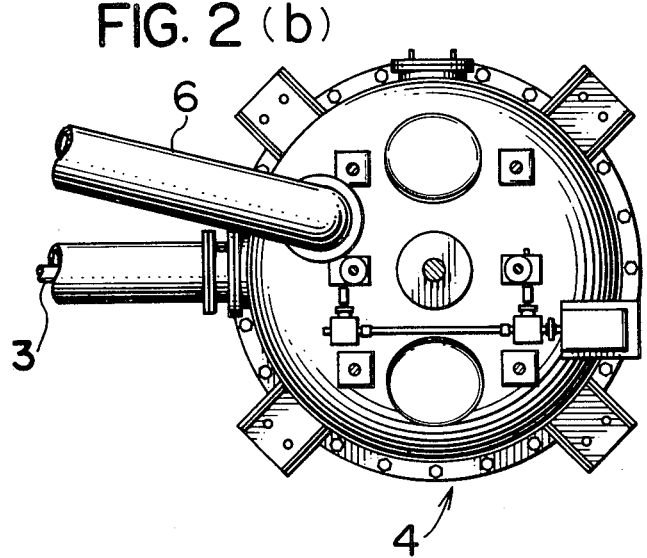
Figure 3:
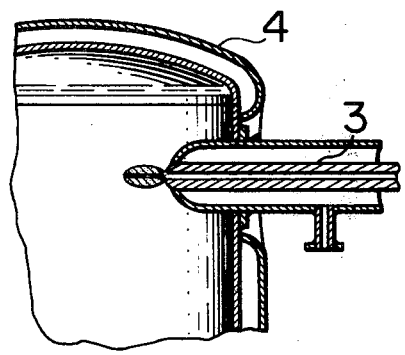

FIGS. 1 and 2(a, b) are schematic views of apparatus used for carrying out a method according to the present invention; and FIGS. 3 to 7 are explanatory views of the operation of the apparatus of FIGS. 1 and 2.

Referring to FIG. 1, numeral 1 indicates a starting solution feed line and numeral 2 a device for quantitatively feeding the starting solution e.g. a quantitative pump or the like. Numeral 3 indicates an elongated heating tube which may be extended in any desirable shape e.g. bent shape, the ratio of its length to its inner diameter being 200-5000. The heating tube 3 is heated above 230° C. from outside by a suitable means. Numeral 4 indicates a separation chamber, and volatile ingredients such as TDI vaporized in the heating tube enter the separation chamber in the form of superheated vapor, while TDI tar enters the separation chamber in the form of highly viscous pitch and is solidified there. The separation chamber is kept at such a temperature that the vapor of TDI or the like is not condensed but that TDI tar is solidified without becoming viscous. For this reason, the separation chamber usually is required to be heated in a jacket and further required to be kept evacuated to the possible highest degree. The vapor of TDI and other volatile ingredients is discharged from the chamber through a pipe 6 connected to a condensor and a vacuum pump (not shown).

Below the separation chamber 4, there is provided a solidified mass take-out device 5 by which TDI tar in solid form is taken out of the vacuum system.

Crude TDI to be treated is quantitatively fed into the heating tube 3 by means of the quantitative feeding device 2. In the heating tube 3, most part of volatile ingredients of the crude TDI, subject to sensible heat and latent heat, is evaporated, and under a certain condition, a part of the resulting vapor is further heated to become superheated vapor. In the heating tube, the TDI tar is present in the form of a highly viscous solution due to the high temperature and TDI remaining therein, and sent to the tube end by the high speed vapor stream. And when spouted into the evacuated separation chamber 4, the TDI tar is condensed at the distal end of the tube due to the temperature drop caused by the evaporation of the remaining very small amount of volatile ingredient and possibly due to the decomposition of TDI tar and the like. By selecting operating conditions as abovementioned, the solidified TDI tar is released and falls down from the distal end of the heating tube every proper time interval in the form of hollow small masses. However, if the release is not easily achieved, a suitable mechanical or other treatment may be used for promoting such release in order to prevent the small masses from growing to be large masses. The solidified mass take-out device 5 may be in any form if it permits the solidified masses to be taken out of the vacuum system.

Referring now to FIG. 2 (where similar numerals have similar meanings to those of FIG. 1), the outlet of the heating tube is located at the lower portion of the separation chamber 4, so that spouted foam TDI tar is gradually accumulated upward from the bottom of the chamber. By stopping the operation of the apparatus at a proper time, actuating the pulverizing device 7 preliminarily provided in the chamber 4 to pulverize the sedimented TDI tar mass and then opening a bottom valve 8, the pulverized TDI tar can be discharged.

In both of the apparatus as shown in FIGS. 1 and 2, the vacuum degree in the separation chamber should be below 200 torr and is preferably 1–50 torr.

Further, in order to achieve the evaporation of TDI at as low as possible temperature and to facilitate the solidification of TDI tar, advantageous is the addition of a solvent e.g. monochlorobenzene, dichlorobenzene or the like which is inert to TDI and preferably has lower boiling point than TDI.

EXAMPLE 1

A stainless steel pipe (of 3m length and 3mm inner diameter) in a jacket was used as a heating tube. The jacket was heated by circulating 300° C. heat transfer fluid. As shown in FIG. 1, the heating tube opened at one end to a starting solution quantitative pump and at the other end to a separation chamber (of 30cm inner diameter and 50cm height) in a jacket. The separation chamber was connected through a condenser to a vacuum pump so as to keep 10 torr vacuum therein.

Figure 4:
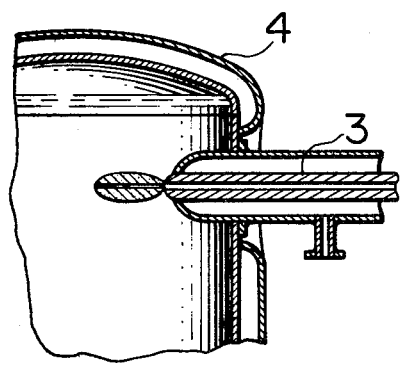
Figure 5:
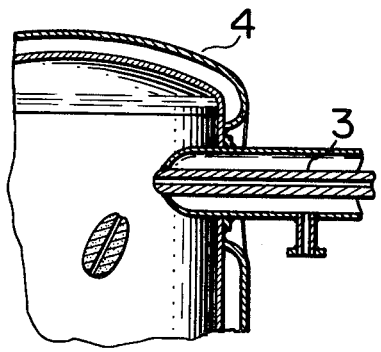

Using such apparatus, the starting solution containing 50% TDI, 45% dichlorobenzene and 5% TDI tar was fed into the heating tube at a rate of 30ml/min. Then, most part of volatile ingredients of the starting solution were evaporated in the heating tube, and by superheating further, the evaporated substances were spouted in the form of superheated vapor into the separation chamber at high speed. By this high speed stream of superheated vapor, TDI tar was sent in the form of highly viscous fluid to the distal end of the heating tube and when the TDI tar entered the separation chamber of lower pressure than the heating tube, it relieved a very small amount of volatile substances remaining therein and was solidified into a doughnut-like shape. By continuing the operation, the solid substance grew into such a shape as shown in FIG. 4, and lastly fell down by gravity off the distal end of the heating tube to the bottom of the separation chamber, whereby the original state was recovered in the tube. The fallen TDI tar was a nonviscous and porous mass (of 1.5cm diameter and about 2.5cm length, having 0.22 specific gravity) and therefore was easily taken out of the bottom of the chamber. Then, this TDI tar mass was analysed to prove that TDI content therein was below 1%. Further analysis resulted in the confirmation that recovered TDI did not contain TDI tar at all.

On the other hand, another starting solution containing 50% TDI, 20% TDI tar and 30% dichlorobenzene was efficiently treated similarly to the abovementioned starting solution.

EXAMPLE 2

Figure 6:
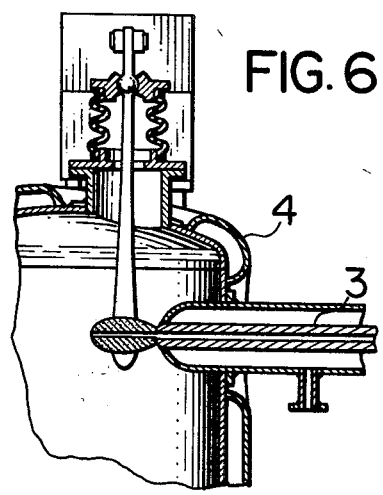
Figure 7:
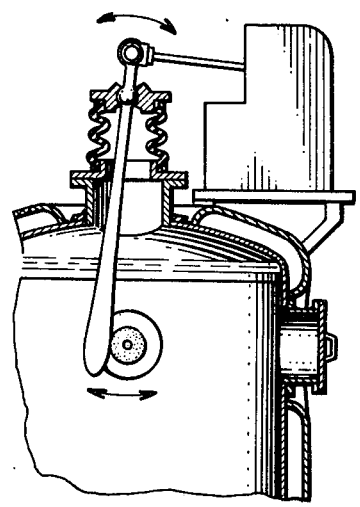

Using the same apparatus as used in Example 1 but with the heat transfer fluid temperature of 320° C. and the vacuum degree of 5 torr, a starting solution containing 95% TDI and 5% TDI tar was treated at a rate of 35ml/min. In this case, the TDI tar mass formed at the distal end of the heating tube did not easily fall down by gravity. Therefore, by operating a scrubbing bar as shown in FIGS. 6 and 7 so as to give a slight shock to the mass already grown into a proper size, the mass (of about 0.20 specific gravity) could be easily dislodged. Similarly to the case of Example 1, the mass was nonviscous and therefore could be easily taken out of the bottom of the chamber, and TDI content was below 1%.

EXAMPLE 3

As a heating tube, a stainless steel pipe (of 15m length and 8mm inner diameter) in a jacket was used. The jacket was heated by circulating 280° C. heat transfer fluid. As shown in FIG. 2, the heating tube opened at one end to a starting solution quantitative pump and at the other end to a separation chamber (of 60cm inner diameter and 50cm height) in a jacket. In the separation chamber, there was provided a pulverizing device 7 which was vertically movable while rotating. Further, the separation chamber was connected through a pipe 6 to a condenser and a vacuum pump so as to keep 3 torr vacuum. At the bottom of the separation chamber there was provided a discharge valve 8 of a large bore.

With this apparatus, a starting solution containing 70% TDI and 30% TDI tar was fed into the heating tube at a rate of 200ml/min. Most part of TDI contained in the starting solution was evaporated into vapor or superheated vapor and spouted into the separation chamber at high speed. Due to the effect of this high speed vapor stream and the high temperature, TDI tar in the form of highly viscous fluid was sent, forming an annular shape stream or a spray stream, to the distal end of the heating tube, and then spouted therefrom into the separation chamber. Here the remaining very small amount of volatile substance was evaporated and possibly the TDI tar was decomposed to become a foamy solidified substance. It could not be absolutely expected from the conventional knowledge that this foamy solidified substance grew while always retaining therein passages for vapor and that by a long time operation it filled the separation chamber. Therefore, after stopping feeding the starting solution before the separation chamber being completely filled with the solid substance, and relieving undesirable vacuum in the chamber to obtain the normal pressure, the solidified mass filled in the chamber was pulverized by the vertically movable pulverizing device 7 and discharged through the discharge valve 8. The TDI content of the resulting solidified substance was below 1%.

What is claimed is:

1. A method for removing tar material from crude tolylene diisocyanate comprising:
   quantitatively feeding a solution consisting of crude tolylene diisocyanate containing tar material or its mixture with an inert organic solvent into the inlet of an elongated heating tube so dimensioned as to have the ratio of its tube length to its inner diameter in a range from about 200 to about 5000 and heated above 230° C., superheating the solution through the elongated heating tube to convert a tolylene diisocyanate of the solution into a superheated vapor in the region of the outlet of the elongated heating tube, spouting the solution thus superheated from the outlet of the heating tube into a separation chamber maintained at a temperature to solidify the tar material while not to condense the vapor of tolylene diisocyanate and under a reduced pressure below 200 torr thereby to obtain a nontacky and pulverizable tar material substantially freed from the tolylene diisocyanate by the sudden cooling thereof through the adiabatic expansion of a small amount of tolylene vapor contained therein.

2. The method of claim 1, in which the temperature in the heating tube is 270°–330° C.; the ratio of the tube length to the inner diameter of the heating tube is 500°–2000°; and the vacuum degree in the separation chamber is 1–30 torr.

3. The method of claim 1, in which by the operation of a scrubbing means provided near the outlet of the heating tube, the tar is obtained in the form of hollow cylindrical small masses.

4. The method of claim 1, in which the outlet of the heating tube opens into the lower portion of the separation chamber, whereby the tar can be obtained in the form of highly porous mass which has been accumulated upward from the bottom of the separation chamber.

* * * * *

UNITED STATES PATENT AND TRADEMARK OFFICE
CERTIFICATE OF CORRECTION

PATENT NO. : 4,138,424

DATED : February 6, 1979

INVENTOR(S) : YOSHIHIRO MAEKAWA ET AL

It is certified that error appears in the above-identified patent and that said Letters Patent are hereby corrected as shown below:

Column 6, line 47, delete "500°-2000°" and insert --500-2000--

*Signed and Sealed this*

*First* Day of *April 1980*

[SEAL]

Attest:

SIDNEY A. DIAMOND

*Attesting Officer*  *Commissioner of Patents and Trademarks*